(12) United States Patent
Fujii

(10) Patent No.: US 7,201,975 B2
(45) Date of Patent: Apr. 10, 2007

(54) ORGANIC LIGHT EMITTING DEVICE

(75) Inventor: Hiroyuki Fujii, Kyoto (JP)

(73) Assignee: Sanyo Electric Co., Ltd., Moriguchi-shi (JP)

( * ) Notice: Subject to any disclaimer, the term of this patent is extended or adjusted under 35 U.S.C. 154(b) by 154 days.

(21) Appl. No.: 10/011,313

(22) Filed: Dec. 11, 2001

(65) Prior Publication Data

US 2002/0071963 A1    Jun. 13, 2002

(30) Foreign Application Priority Data

Dec. 13, 2000    (JP)    ............................. 2000-379404

(51) Int. Cl.
*H01L 51/54*    (2006.01)
*H05B 33/14*    (2006.01)

(52) U.S. Cl. ...................... 428/690; 428/917; 313/504; 313/506; 257/102; 257/E51.044; 257/E51.047; 257/E51.051; 257/103

(58) Field of Classification Search ................ 428/690, 428/917; 313/504, 506; 257/102, 103
See application file for complete search history.

(56) References Cited

U.S. PATENT DOCUMENTS

| | | | |
|---|---|---|---|
| 4,727,003 | A | 2/1988 | Ohseto et al. |
| 4,769,292 | A * | 9/1988 | Tang et al. .................. 428/690 |
| 5,061,569 | A | 10/1991 | VanSlyke et al. |
| 5,294,810 | A * | 3/1994 | Egusa et al. ................... 257/40 |
| 5,698,858 | A | 12/1997 | Borner et al. |
| 5,756,224 | A | 5/1998 | Borner et al. |
| 5,779,937 | A | 7/1998 | Sano et al. |
| 5,932,896 | A | 8/1999 | Sugiura et al. ................ 257/94 |
| 5,935,720 | A | 8/1999 | Chen et al. |
| 5,935,721 | A * | 8/1999 | Shi et al. ..................... 428/690 |
| 6,064,079 | A | 5/2000 | Yamamoto et al. .......... 257/101 |
| 2001/0053462 | A1* | 12/2001 | Mishima ...................... 428/690 |
| 2002/0034655 | A1* | 3/2002 | Watanabe et al. ............ 428/690 |
| 2002/0045061 | A1* | 4/2002 | Hosokawa ................... 428/690 |
| 2005/0222429 | A1 | 10/2005 | Hosokawa |
| 2006/0046098 | A1 | 3/2006 | Hosokawa |

FOREIGN PATENT DOCUMENTS

| | | |
|---|---|---|
| JP | 62-74986 | 4/1987 |
| JP | 3-232856 | 10/1991 |
| JP | 07-045902 | 2/1995 |
| JP | 8-157815 | 6/1996 |
| JP | 8-315983 | 11/1996 |
| JP | 8-319482 | 12/1996 |
| JP | 09-246651 | 9/1997 |
| JP | 10-093198 | 4/1998 |
| JP | 10-150240 | 6/1998 |
| JP | 10-303502 | 11/1998 |
| JP | 10-308281 | 11/1998 |
| JP | 10-321962 | 12/1998 |
| JP | 11-031866 | 2/1999 |
| JP | 11-214800 | 8/1999 |
| JP | 11-329734 | 11/1999 |
| JP | 2000-21572 | 1/2000 |
| JP | 2001-313178 | 11/2001 |
| JP | 2001-313179 | 11/2001 |
| WO | WO 00-70655 | 11/2000 |
| WO | WO 01-72927 | 10/2001 |

OTHER PUBLICATIONS

Baldo et al., "Very high-efficiency green organic light-emitting devices based on electrophosphorescence", Applied Physics Letters, vol. 75, No. 1, pp. 4-6, Jul. 1999.*

Masamichi Ikai et al.; *Highly efficient phosphorescence from organic light-emitting devices with an exciton-block layer*, Applied Physics Letters; vol. 79, No. 2, pp. 156-158; Jul. 2001.

Brian W. D'Andrade et al.; *High- efficiency yellow double-doped organic light-emitting devices based on phosphor-sensitized fluorescence*, Applied Physics Letters; vol. 79, No. 7, pp. 1045-1047; Aug. 2001.

Chihaya Adachi et al.; *Efficient electrophosphorescence using a doped ambipolar conductive molecular organic thin film*, Organic Electronics; vol. 2, No. 1, pp. 37-43; Mar. 2001.

Yasuhiko Shirota et al.; *Organic materials for electronic and optoelectronic devices*, Journal of Materials Chemistry; vol. 10, No. 1, pp. 1-25; Jan. 2000.

Teruichi Watanabe et al.; *Optimization of emitting efficiency in organic LED cells using Ir Complex*, Synthetic Metals; vol. 122, pp. 203-207; May 2001.

Yoshiyuki Kuwabara et al.; *Thermally stable multilayered organic Electroluminescent devices using novel starburst molecules, 4,4',4"-Tri (N-carbazolyl)triphenylamine (TCTA) and 4, 4', 4"-Tris (3-methylphenylphenylamino)triphenylamine (m-MTDATA), as hole-transport materials*, Adv. Materials; vol. 6, No. 9, pp. 677-679; 1994.

C. H. Chen et al.; *Recent developments in the synthesis of red dopants for $Alq_3$ hosted electroluminescence*, Thin Solid Films; vol. 363, pp. 327-331; Mar. 2000.

Tetsuo Tsutsui et al.; *High quantum efficiency in organic light-emitting devices with iridium-complex as a triplet emissive center*, Japanese Journal of Applied Physics; vol. 38, pp. L1502-L1504; 1999.

(Continued)

*Primary Examiner*—Marie Yamnitzky
(74) *Attorney, Agent, or Firm*—Westerman, Hattori, Daniels & Adrian, LLP

(57) ABSTRACT

A hole injection layer, a hole transport layer, a mixture luminescent layer, a hole blocking layer, an electron injection layer and a cathode are formed on an anode. The mixture luminescent layer includes TCTA as a luminescent substance, Ir(ppy) as a substance emitting light through a triplet excited state, and DCJTB as a luminescent substance emitting the light of a spectral component in the wavelength range of red.

22 Claims, 2 Drawing Sheets

OTHER PUBLICATIONS

J. Kido et al.; *White light-emitting organic electroluminescent devices using the poly(N-vinylcarbazole) emitter layer doped with three fluorescent dyes*, Appl. Phys. Lett.; vol. 64, No. 7, pp. 815-817; Feb. 14, 1994.

Notification of Reasons for Refusal in the counterpart Japanese Application (JP2000-379404) dated May 9, 2006 and its English translation.

D.F. O'Brien et al., *Improved energy transfer in electrophosphorescent devices*, Applied Physics Letters, vol. 74, No. 3, pp. 442-444, Jan. 18, 1999.

Chihaya Adachi et al., *Electroluminescence mechanisms in organic light emitting devices employing a europium chelate doped in a wide energy gap bipolar conducting host*, Journal of Applied Physics, vol. 87, No. 11, pp.8049-8055, Jun. 1, 2000.

M.A. Baldo et al., *High-efficiency fluorescent organic light-emitting devices using a phosphorescent sensitizer*, Nature, vol. 403, pp. 750-753, Feb.17, 2000.

C.J. Curtin et al., *Scaling of FED Display Technology to Large Area Displays*, Society for Information Display International Symposium Digest of Technical Papers, vol. XXXI (ISSN0000-0966X), pp. 1263-1265, 2000.

Takeshi Sano et al., *Novel Europium Complex for Electroluminescent Devices with Sharp Red Emission*, Jpn. J. Appl. Phys. vol. 34 (1995), Part 1, No. 4A, pp.1883-1887, Apr. 1995.

M.A. Baldo et al., *Highly efficient phosphorescent emission from organic electroluminescent devices*, Nature, vol. 395, pp. 151-154, Sept. 10, 1998.

Decision Refusal in the counterpart Japanese Application (JP2000-379404) dated Aug. 1, 2006 and its English translation.

* cited by examiner

ORGANIC LIGHT EMITTING DEVICE

BACKGROUND OF THE INVENTION

1. Field of the Invention

The present invention relates to organic light emitting devices such as organic electroluminescence devices (hereinafter referred to as organic EL devices) and, particularly, to an organic light emitting device which emits a spectral component in the wavelength range of blue or a spectral component in the range of a wavelength shorter than that of blue, and is capable of obtaining white light emission or blue light emission.

2. Description of the Background Art

In recent years, requirements are increasing for thin display devices having a thickness of approximately several mm and capable of providing full-color display with the advance of information technology (IT). As such thin display devices, organic EL devices have been developed.

Three methods are roughly proposed as means for realizing full-color display. The first method is such that a large number of light emitting devices are arranged which emit respective monochromatic lights of red, green and blue, which are three primary colors of light. The second method is to adopt a combination of a white light emitting diode and a color filter which allows transmission of monochromatic lights of three primary colors of light. The third method is to adopt a light emitting diode which emits ultraviolet light or blue light and wavelength converting means for wavelength-converting the light from the light emitting diode into monochromatic lights of three primary colors of light. It is uncertain at present which method is superior to others.

In general, while it is comparatively easy to realize highly efficient organic light emitting devices which emit green light, it is difficult to realize those which emit red light. It is more difficult to realize organic light emitting devices which emit blue light and white light.

Requirements are now made for light emitting devices emitting blue light and white light in each of the above mentioned methods for achieving full-color display as described above. Thus, a demand is increasing for achieving an organic light emitting device which emits a spectral component in the wavelength range of blue or a spectral component in the wavelength range of a shorter wavelength than that of blue, and is capable of obtaining blue light or white light, by employing any one of the above described methods.

For example, Forrest, Stephen R. et al. discloses in *Appl. Phys. Lett.*, 1999, 75(1), pp. 4–6 an organic EL device emitting green light which has a mixture luminescent layer made by mixing fac-tris(2-phenylpyridine)iridium (hereinafter abbreviated as Ir(ppy)) being a green phosphorescence emitting substance into 4,4'-bis(carbazol-9-yl)-biphenyl (hereinafter abbreviated as CBP) at a concentration of 1 to 12 mass %.

The document describes that a maximum luminous efficiency was attained in the organic EL device when the concentration of Ir(ppy) in the mixture luminescent layer was 6 mass %, resulting in such properties as a luminescence peak wavelength being 510 nm, a full-width at half maximum value (FWHM value) of a luminescence peak being 70 nm, and a chromaticity coordinate of Commission International d'Eclairage (CIE) being (x=0.27, y=0.63).

The document mentions that a blue emitting component is negligible which is considered to be provided from a singlet excited state of CBP even though a current density is raised to 100 mA/cm², and thus, complete energy transfer occurs from CBP to Ir(ppy) in this organic EL device (Refer to FIG. 4 in the document). It is thus impossible to obtain blue light emission or white light emission in the organic EL device by employing the technology disclosed in the above described document.

A simplified molecular formula for CBP is represented by $C_{36}H_{24}N_2$ where one molecule includes 36 carbon atoms, 2 nitrogen atoms and 24 hydrogen atoms. A molar mass of CBP is 484.60 g/mol and its melting point is 282° C. to 283° C. The wavelength of an absorption edge on the side of the longest wavelength in an optical absorption spectrum in a visible light range of CBP is 400 nm. A structural formula for CBP is represented by a chemical formula (1) shown below.

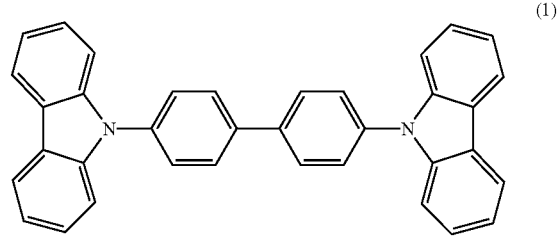

(1)

Moreover, Forrest, Stephen R. et al. disclose in *Appl. Phys. Lett.*, 1999, 74(3), pp. 442–444 an organic EL device emitting red light which has a mixture luminescent layer made by mixing 2,3,7,8,12,13,17,18-octaethenyl-21H,23H-porphine platinum (II) (hereinafter abbreviated as PtOEP) being a red phosphorescence emitting substance into CBP at a concentration of 6 mass %.

In the disclosed organic EL device, a red emitting component with a 650 nm luminescence peak wavelength, which is considered to be provided from a triplet excited state of PtOEP, covers most of the photons discharged from the device, while a red emitting component with a 580 nm luminescence peak wavelength, which is considered to be provided from the singlet excited state of PtOEP, is not detected. In this organic EL device, however, any blue emitting component is not detected, which is considered to be provided from the singlet excited state of CBP (Refer to FIG. 3 in the document). It is thus impossible to obtain blue light emission or white light emission in the organic EL device by employing such technology as disclosed in the described document.

In addition, Forrest, Stephen R. et al. disclose in *Appl. Phys.*, 2000, 87(11), pp. 8049–8055 an organic EL device having a mixture luminescent layer made by mixing tris (thenoyltrifluoroacetone)(1,10-phenanthroline)europium (hereinafter referred to as Eu(tta)₃phen), which is a compound similar to europium (III)-phenanthroline-tri-thenoyl-trifluoro-acetylacetonate (hereinafter abbreviated as Eu(ttfa)₃ phentp) emitting red light, into CBP to a concentration of 1 mass %.

In the disclosed organic EL device, a red light emission with a 612 nm luminescence peak wavelength is obtained which is considered to be provided from the triplet excited state of Eu(tta)₃phen. When a current density is 100 mA/cm², in this organic EL device, a 505 cd/m² luminance is attained, and a 0.22% external quantum efficiency and a 0.505 cd/A current luminous efficiency are obtained.

FIG. 1 in the described document shows respective energy levels of constituent materials. In this case, the energy level of Eu(tta)₃phen is unclear; however, it is described that the level of a lowest unoccupied molecular orbital (LUMO) of CBP is 3.2 eV and the level of a highest occupied molecular orbital (HOMO) is 6.3 eV. It is thus evaluated that an energy gap between LUMO and HOMO is 3.1 eV. An ionization potential of CBP is considered to be 6.3 eV equal to the level of HOMO.

The organic EL device disclosed here is, however, the red light emitting device as described above. Therefore, it is impossible to obtain blue light emission or white light emission in the organic EL device by employing such technology as disclosed in the described document.

Moreover, Forrest, Stephen R. et al. disclose in *Nature*, 2000, 403, 6771, pp. 750–753 an organic EL device fabricated by forming a first type of mixture luminescent layer which is made by mixing 2-methyl-6-[2-(2,3,6,7-tetrahydro-1H,5H-benzo[ij]quinolizin-9-yl)ethenyl]-4H-pyran-4-ylidene] propane-dinitrile (hereinafter abbreviated as DCM2) being a red fluorescence emitting substance into CBP at a concentration of 1 mass %; forming a second type of mixture luminescent layer which is made by mixing the above described Ir(ppy) being a green phosphorescence emitting substance into CBP at a concentration of 10 mass %; and forming a stacked mixture luminescent layer which is made by stacking five pairs of the first and second types of mixture luminescent layers (i.e., 10 layers in total), with each pair including the first type and the second type of mixture luminescent layers.

The above described organic EL device exhibits such results that a red emitting component with a 590 nm luminescence peak wavelength which is considered to be produced from the singlet excited state of DCM2 covers 80% of the photons discharged from the device, and that a green emitting component with a 500 nm luminescence peak wavelength which is considered to be produced from the triplet excited state of Ir(ppy) covers the remaining approximately 20% of the photons. As described above, in this case, a blue emitting component with a 400 nm luminescence peak wavelength which is considered to be produced from the singlet excited state of CBP is hardly detected (Refer to FIG. 3 in the document). It is thus impossible to obtain blue light emission or white light emission in the organic EL device by employing the technology disclosed in this document.

A simplified molecular formula for DCM2 is $C_{23}H_{21}ON_3$, and its molar mass is 355.43 g/mol. A structural formula for DCM2 is represented by a formula (11) shown below.

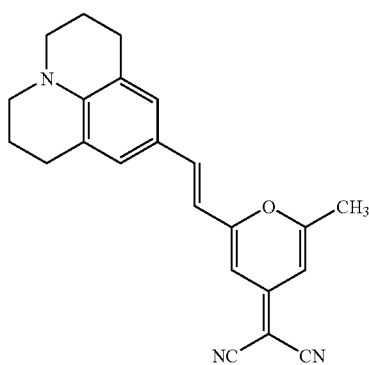

(11)

On the other hand, Japanese Patent Laid Open No. 8-157815 discloses an organic EL device emitting white light in which a thin film constituted by a copolymer of a coumarin derivative with a specified structure and N-vinylcarbazole, and fluorescent dye is formed as a luminescent layer. In this case, the copolymer contains 0.01 to 50 mole % of the coumarin derivative, and an average molecular weight of the copolymer is 1,000 to 1,000,000 in terms of polystyrene.

As for a device fabricated in Example 1 of the foregoing Japanese document, it is described that when a 15 V DC voltage was applied to the fabricated device in the atmosphere, then approximately 10 mA/cm$^2$ of electric currents flowed, and uniform and stable white surface-emission with a 300 cd/m$^2$ luminance was obtained. Therefore, a current luminous efficiency at this time is evaluated as approximately 3.0 cd/A. As for a device fabricated in Example 2, it is described that when a 15 V DC voltage was applied to the fabricated device in the atmosphere, then approximately 50 mA/cm$^2$ of electric currents flowed, and uniform and stable white surface-emission with a 400 cd/m$^2$ luminance was obtained. Therefore, a current luminous efficiency at this time is evaluated as approximately 0.8 cd/A.

In addition, the Japanese document discloses in FIG. 1 an emission spectrum of the device of Example 2. In this case, the highest luminescence peak is viewed around a 440 nm wavelength, and the second luminescence peak is viewed around a 560 nm wavelength, as shown in FIG. 1.

However, the above described document makes no description as to CIE chromaticity coordinate values representing specific hues, nor the life or the heat resistivity of light emitting devices. Also, the technology disclosed in the document allows achievement of white emission, but not blue emission in the disclosed organic EL device.

In a method disclosed in the foregoing document, a luminescent layer is formed by spin coating a toluene solution including a copolymer and a fluorescence dye over a substrate at 6000 rpm, and then drying the coated substrate at 50° C. under a 10$^{-1}$ Pa reduced pressure, thereby forming a thin film constituted by the copolymer and the fluorescence dye.

It is, in general, considered difficult to make a thin film of polymer by vacuum vapor deposition. Thus, there is a disadvantage that in order to form a luminescent layer by making a thin film of polymer, the formation of the thin film must be made by spin coating using such harmful organic solvent as toluene, as described above. Further, the foregoing thin film formation method by spin coating the copolymer has a disadvantage that it is difficult to form a thin film with a uniform thickness over a large substrate.

SUMMARY OF THE INVENTION

An object of the present invention is to provide an organic light emitting device with excellent luminous efficiency which emits a spectral component in a wavelength range of blue or a spectral component in a wavelength range of a shorter wavelength than that of blue and allows emission of blue or white light.

An organic light emitting device according to one aspect of the present invention includes an anode, a cathode and a luminescent substance placed between the anode and the cathode, wherein the luminescent substance includes at least a molecular substance in which an absorption edge of the longest wavelength in an optical absorption spectrum in a visible light range is located at a shorter wavelength than the wavelength of 4,4'-bis(carbazol-9-yl)-biphenyl represented by a structural formula (1) shown below.

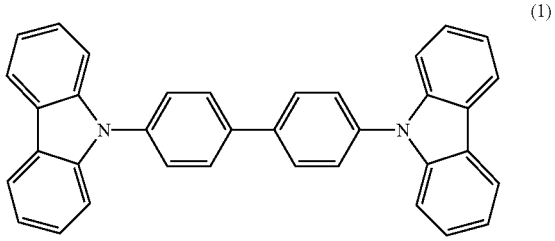

(1)

In the organic light emitting device in accordance with the present invention, since the luminescent substance includes the foregoing molecular substance, the organic light emitting device is allowed to emit the spectral component in the wavelength range of blue or the spectral component in the wavelength range of the shorter wavelength than that of blue. This effects accomplishment of blue emission in such an organic light emitting device.

The luminescent substance may further include a substance emitting through a triplet excited state. In this case, blue emission is obtained from the molecular substance, and emission is also obtained from the substance emitting through the triplet excited state. Thus, combination of both emission allows white emission. Accordingly, the organic light emitting device capable of emitting white light can be realized in this case.

Since the substance emitting light through the triplet excited state is included as the luminescent substance in this case, this substance can emit light through the triplet excited state, which is not normally utilized effectively without taking part in emission.

Since emission can be made by effective use of the triplet state, which has not normally used effectively, in this case, luminous efficiency can greatly be enhanced in the substance emitting light through the triplet excited state.

As for the molecular substance, the absorption edge wavelength on the side of the longest wavelength in the optical absorption spectrum in the visible light range is preferably below 400 nm. The absorption edge wavelength is preferably 310 nm or more, and the absorption edge wavelength of 365 nm to 390 nm is particularly preferable. Such a molecular substance allows emission of a spectral component of the wavelength of blue or a spectral component of a shorter wavelength than that of blue.

An ionization potential of the molecular substance is preferably lower than that of the above described 4,4'-bis(carbazol-9-yl)-biphenyl. The ionization potential of the molecular substance is preferably 6.2 eV or less. The ionization potential is preferably 5.0 eV or more. Especially, the ionization potential of from 5.3 eV to 5.9 eV is preferable.

In the molecular substance with the above ionization potential, since energy barriers become greater in transportation of holes injected from the anode, the holes can be stored in the molecular substance. Thus, coupling of the holes and electrons can be made with high efficiency. This makes it possible to enhance luminous efficiency in the molecular substance as described above.

A molar mass of the molecular substance is preferably 486 g/mol or more. The molar mass is preferably 1800 g/mol or less, and particularly, the molar mass of from 588 g/mol to 1190 g/mol is preferable. Such a molecular substance with large molar mass achieves improved heat resistivity. This makes it possible to enhance the heat resistivity of the organic light emitting device having the luminescent substance including such a molecular substance.

It is preferred that 3 or more nitrogen atoms are contained in one molecule of the molecular substance. 7 or less nitrogen atoms per molecule are preferable in the molecular substance, and particularly, 4 to 5 nitrogen atoms per molecule are preferable.

Since a large number of nitrogen atoms are contained in one molecule of such a molecular substance, this improves transportability of holes and increases luminous efficiency and heat resistivity. Accordingly, the luminous efficiency and the heat resistivity are enhanced in the organic light emitting device having the luminescent substance including the above described molecular substance.

It is preferable that the molecular substance contains 37 or more carbon atoms per molecule. The carbon atoms to be contained in one molecule of the molecule substance are preferably 135 or less, and 44 to 89 carbon atoms are especially preferable.

Since a large number of carbon atoms are contained in one molecule of such a molecular substance, heat resistivity can be increased. This makes it possible to enhance the heat resistivity of the organic light emitting device having the luminescent substance including such a molecular substance.

It is preferable that the melting point or the glass transition temperature of the molecular substance is higher than that of the above described 4,4'-bis(carbazol-9-yl)-biphenyl. The molecular substance with a high melting point or high glass transition temperature is formed as amorphous solids in the range of temperature below the glass transition temperature and is maintained in an amorphous state.

Accordingly, it becomes possible, in the organic light emitting device having the luminescent substance including such a molecular substance, to inhibit the generation of deviations in electric conductivity or the generation of electrical short-circuit resulting from crystallization in the luminescent substance. Thus, even if the temperature of the periphery of the device rises to the range of high temperatures below the glass transition temperature, the organic light emitting device having such a luminescent substance is not destroyed, resulting in higher heat resistivity of the organic light emitting device.

The molecular substance may have such a structure represented by a general formula (2) shown below.

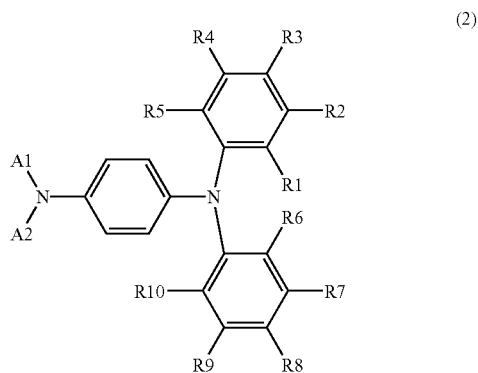

(2)

In the above formula, R1 to R10 are identical to or different from one another representing hydrogen atoms or substituents. R1 and R6 may be bonded to each other to form a ring. Adjacent ones of R1 to R5 and adjacent ones of R6 to R10 may be bonded to each other to form respective rings. A1 and A2 are identical to or different from each other representing hydrogen atoms or substituents.

In the molecular substance having the above structure, at least one of A1 and A2 may be a group represented by a general formula (3) shown below.

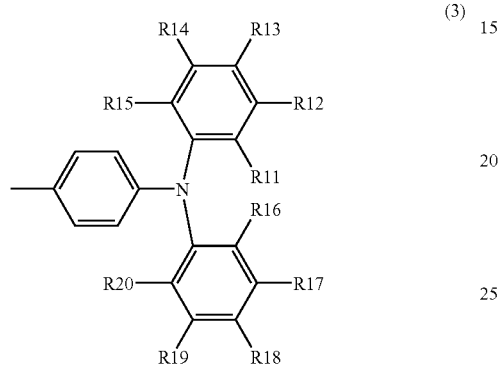

(3)

In the above formula, R11 to R20 are identical to or different from one another representing hydrogen atoms or substituents. R11 and R16 may be bonded to each other to form a ring. Adjacent ones of R11 to R15 and adjacent ones of R16 to R20 may be bonded to each other to form respective rings. R11 to R20 may be identical to or different from R1 to R10.

It is preferable that the molecular substance having the above structure includes a carbazol-9-yl structure represented by a general formula (4) shown below.

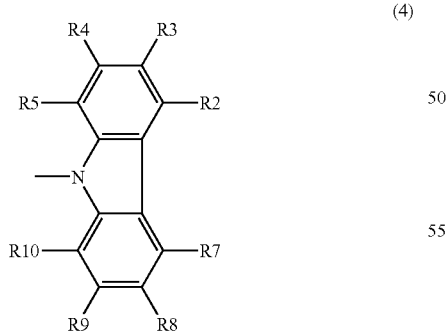

(4)

In the above formula, R2 to R5 and R7 to R10 are the same as the foregoing.

It is preferable that the molecular substance having the above structure includes a carbazol-9-yl structure represented by a general formula (5) as shown below.

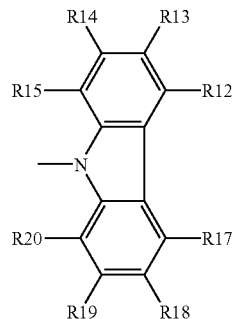

(5)

In the above formula, R12 to R15 and R17 to R20 are the same as the foregoing.

It is preferable that the molecular substance having the above structure includes three or more carbazol-9-yl structures per molecule.

In particular, the molecular substance is preferably 4,4',4''-tri(N-carbazolyl)triphenylamine represented by a formula (6) shown below.

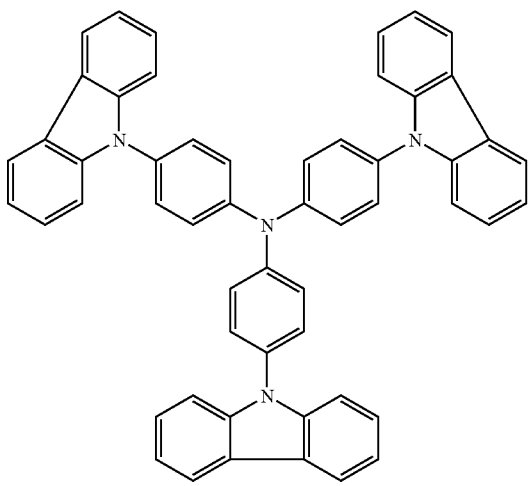

(6)

As for the above described 4,4',4''-tri(N-carbazolyl)triphenylamine, an absorption edge wavelength on the side of the longest wavelength in an optical absorption spectrum in a visible light range is below 400 nm, specifically 390 nm, and it is possible to emit a spectral component of the wavelength of blue or a spectral component of a shorter wavelength than that of blue. Further, highly efficient blue emission can be made because of its low ionization potential.

Therefore, blue emission can be achieved at excellent luminous efficiency in the organic light emitting device having the luminescent substance including the above described 4,4',4''-tri(N-carbazolyl)triphenylamine as the molecular substance.

Moreover, the above described 4,4',4''-tri(N-carbazolyl)triphenylamine has a large number of nitrogen atoms and carbon atoms included per molecule, and has a large molar mass and a high glass transition temperature. This allows an improvement in heat resistivity of the organic light emitting device having the luminescent substance including the above 4,4',4"-tri(N-carbazolyl)triphenylamine as the molecular substance.

The substance emitting through the triplet excited state may be a substance including chemical elements of atomic number 56 or more. The substance emitting through the triplet excited state may be a substance including chemical elements of atomic number 76 or more.

The substance emitting through the triplet excited state may include at least one type of element selected from the group consisting of Group 8 elements, Group 9 elements, Group 10 elements and Group 11 elements of the Periodic Table of Elements. The substance emitting through the triplet excited state may include at least one type of element selected from the group consisting of osmium, iridium, platinum and gold. It is especially preferable that such a substance includes iridium.

It is preferable that the substance emitting through the triplet excited state has a structure represented by a general formula (7) shown below.

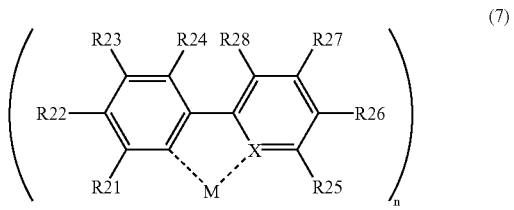

In the above formula, M represents a metal atom, and X represents a nonmetal atom. R21 to R28 are identical to or different from one another representing hydrogen atoms or substituents. R24 and R28 may be bonded to each other to form a ring. Adjacent ones of R21 to R24 may be bonded to each other to form respective rings, and adjacent ones of R25 to R28 may be bonded to each other to form respective rings. n represents an integer of from 1 to 4.

It is particularly preferable that the substance emitting through the triplet excited state is fac-tris(2-phenylpyridine) iridium represented by a formula (8) as shown below.

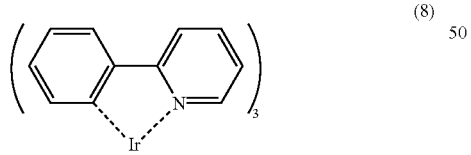

The above described fac-tris(2-phenylpyridine)iridium can emit green light at excellent luminous efficiency by effective use of the triplet excited state. This makes it possible to obtain white emission in the organic light emitting device by mixing the green emission of fac-tris(2-phenylpyridine)iridium and the blue emission of the foregoing molecular substance.

The substance emitting through the triplet excited state may emit the light of spectral components in the wavelength range of green and/or red. In this case, it becomes possible to obtain white emission from the organic light emitting device by mixing the emission from the substance emitting through the triplet excited state and the blue emission from the molecular substance.

The luminescent substance may further include a luminescent substance emitting the light of a spectral component in the wavelength range of red. In an organic light emitting substance including such a luminescent substance emitting red light, it becomes possible to obtain white emission by mixing the blue emission from the molecular substance, the emission from the substance emitting through the triplet excited state and the emission from the red emitting substance.

It is preferable that the luminescent substance which emits the light of the spectral component in the wavelength range of red has a molar mass of not less than 356 g/mol nor more than 726 g/mol. It is particularly preferable that that luminescent substance has a molar mass of from 397 g/mol to 454 g/mol.

As for the luminescent substance emitting the light of the spectral component in the wavelength range of red, it is preferable that the number of carbon atoms per molecule is not less than 24 nor more than 35, particularly from 26 to 33.

Since such a luminescent substance includes large-sized molecules, it is possible to obtain an excellent spectral component in the wavelength range of red. Also, the red emitting substance having large-sized molecules has such properties that it easily sublimes even if its molecules are large in size. Therefore, the red emitting device can be formed in the form of thin films by sublimation.

It is preferable that the luminescent substance emitting the light of the spectral component in the wavelength range of red has a structure represented by a general formula (9) shown below.

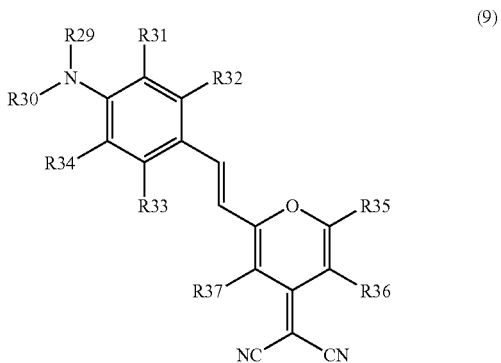

In the above formula, R29 to R37 are identical to or different from one another representing hydrogen atoms or substituents. Adjacent ones of R29, R30, R31 and R34 may be bonded to each other to constitute respective rings. Adjacent R31 and R32, R33 and R34, and R35 and R36 may be bonded to each other to form respective rings.

The luminescent substance emitting the light of the spectral component in the wavelength range of red is preferably 2-(1,1-Dimethylethyl)-6-(2-(2,3,6,7-tetrahydro-1,1,7,7-tetramethyl-1H,5H-benzo(ij)quinolizin-9-yl)ethenyl)-4H-pyran-4H-ylidene)propanedinitrile (hereinafter abbreviated as DCJTB) represented by a formula (10) shown below.

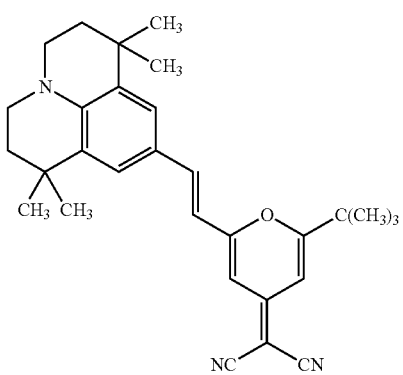

(10)

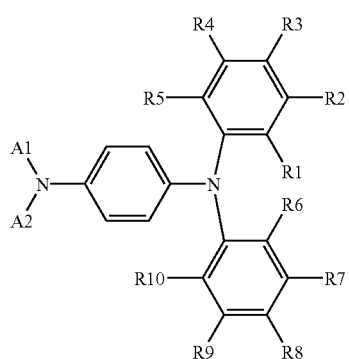

(2)

In the above DCJTB, it becomes possible to achieve excellent red emission of a spectral component at excellent luminous efficiency. This makes it possible to obtain white emission at excellent luminous efficiency in the organic light emitting device by mixing the red emission of DCJTB, the blue emission of the molecular substance and the emission of the substance emitting through the triplet excited state.

The luminescent substance is preferably formed by a vacuum vapor deposition method. In that case, for example, the luminescent substance is sublimated to form a layer composed of the luminescent substance by the vacuum vapor deposition method. The formation of the luminescent substance by vacuum vapor deposition facilitates the formation of the luminescent substance with a uniform thickness without use of any detrimental organic solvent.

The organic light emitting device may further include a luminescent layer provided between the anode and the cathode, and the luminescent layer may include a luminescent substance. In the organic light emitting device having such structure, blue light or white light can be obtained at excellent luminous efficiency.

The foregoing and other objects, features, aspects and advantages of the present invention will become more apparent from the following detailed description of the present invention when taken in conjunction with the accompanying drawings.

DISCRIPTION OF THE PREFERRED EMBODIMENTS

Figure 1:
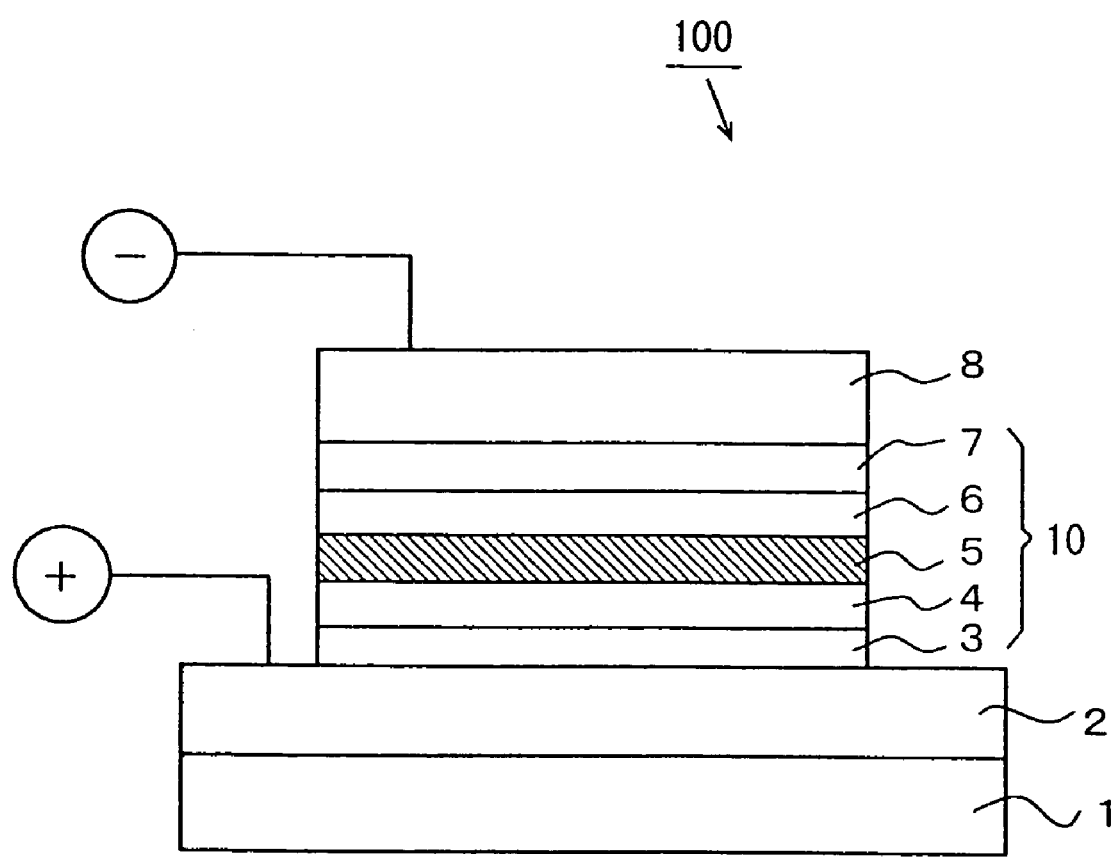
FIG. 1 is a schematic cross-sectional view of an organic EL device in Example 1 of the present invention.

An organic light emitting device according to the present invention includes a luminescent substance having a structure represented by a general formula (2) between a pair of an anode and a cathode.

In the above formula, R1 to R10 are identical to or different from one another representing hydrogen atoms or substituents. The substituents represented by R1 to R10 are, for example, an alkyl group (a $C_{1-6}$ alkyl group such as a methyl group, an ethyl group, a t-butyl group and the like), a cycloalkyl group (a $C_{3-10}$ cycloalkyl group such as a cyclohexyl group and the like) and an aryl group (a $C_{6-18}$ aryl group such as a phenyl group, a naphthyl group, a biphenyl group, a terphenyl group and the like) and the like.

R1 and R6 may be bonding sites which are bonded together to form a carbazole ring or may form other rings, e.g., 6 to 10 membered rings.

Adjacent ones of R1 to R5 and adjacent ones of R6 to R10 may be bonded to each other to form respective rings. For example, they may form a naphthyl group, a phenanthryl group and the like.

A1 and A2 are identical to or different from each other representing hydrogen atoms or substituents. The substituents represented by A1 and A2 are, for example, a phenyl group, a naphthyl group, a p-(diphenylamino)phenyl group, a p-(carbazol-9-yl)phenyl group and the like.

It is especially preferable that such A1 and A2 are substituents forming a conjugated system such as a phenyl group, a naphthyl group and the like.

The organic light emitting device according to the present invention may further include as a luminescent substance, a substance which has a structure represented by a general formula (7) shown below and emits light through a triplet excited state.

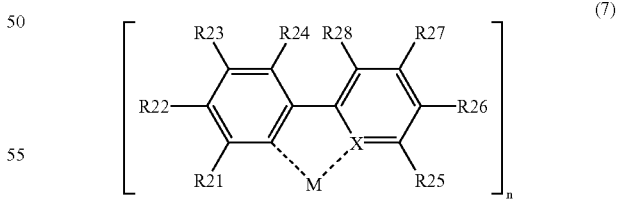

(7)

In the above formula, a nonmetal atom represented by X is normally a hetero atom (a nitrogen atom, an oxygen atom, a sulfur atom and the like), and it is particularly preferable that X is a nitrogen atom. M represents a metal atom such as iridium and the like. In this case, n represents an integer of from 1 to 4.

R21 to R28 are identical to or different from one another representing hydrogen atoms or substituents. The substituents represented by R21 to R28 are, for example, an alkyl group (a $C_{1-6}$ alkyl group such as a methyl group, an ethyl group, a t-butyl group and the like), a cycloalkyl group (a $C_{3-10}$ cycloalkyl group such as a cyclohexyl group and the like), an aryl group (a $C_{6-10}$ aryl group such as a phenyl group, a naphthyl group and the like) and the like.

R24 and R28 may be bonding sites which are bonded to each other forming, e.g., 6 to 10 membered rings.

Adjacent ones of R21 to R24 and adjacent ones of R25 to R28 may be bonded to each other to form respective rings. They may form, for example, a naphthyl group, a phenanthryl group and the like.

Furthermore, the organic light emitting device according to the present invention may include as a luminescent substance, a substance which has a structure represented by a general formula (9) shown below and emits light of a spectral component of the wavelength of red.

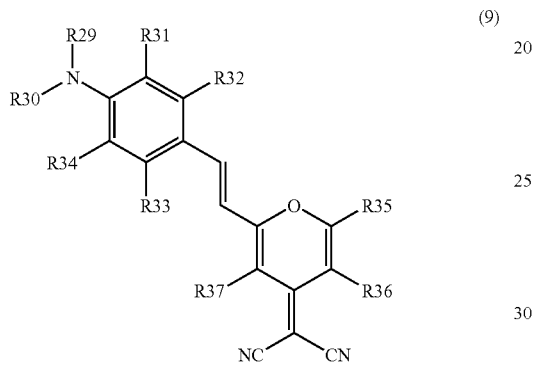

(9)

In the above formula, R29 to R37 are identical to or different from one another representing hydrogen atoms or substituents. The substituents represented by R29 to R37 are, for example, an alkyl group (a $C_{1-6}$ alkyl group such as a methyl group, an ethyl group, a t-butyl group and the like), a cycloalkyl group (a $C_{3-10}$ cycloalkyl group such as a cyclohexyl group and the like), an aryl group (a $C_{6-10}$ aryl group such as a phenyl group, a naphthyl group and the like) and the like.

In particular, the alkyl group represented by R35 may be a $C_{1-10}$ alkyl group such as a methyl group, an ethyl group, a propyl group, an isopropyl group, a butyl group, a t-butyl group, a hexyl group and the like.

Adjacent R31 and R32, adjacent R33 and R34, adjacent R35 and R36 may be bonded to each other to form respective rings. They may form, for example, a naphthyl group, a phenanthryl group and the like.

R29 and R31 may be bonded to each other to form 6 to 8 membered rings. R30 and R34 may be bonded to each other to form 6 to 8 membered rings. Adjacent ones of R29, R30, R31 and R34 may be bonded to each other to form respective rings such as julolidine rings, julolidino-substituted rings and the like.

EXAMPLES

Example 1

FIG. 1 is a schematic cross-sectional view of an organic EL device in Example 1 of the present invention.

In fabrication of an organic EL device 100 shown in FIG. 1, an anode 2 composed of $In_2O_3$—$SnO_2$ (ITO) is formed in advance on a glass substrate 1. A hole injection layer 3, a hole transport layer 4, a mixture luminescent layer 5, a hole blocking layer 6 and an electron injection layer 7 are formed in turn on the anode 2 to form an organic thin film layer 10 by a vapor deposition method at a vacuum degree of $10^{-4}$ Pa order. Further, a cathode composed of an alloy of indium and magnesium (Mg:In) is formed on the organic thin film layer 10.

Description will now be made on the details of the method of forming the organic thin film layer 10.

In the formation of the organic thin film layer 10, first of all, the hole injection layer 3 composed of (3-methylphenylphenylamino)triphenylamine (hereinafter abbreviated as MTDATA) represented by a formula (12) shown below is formed on the surface of the anode 2 composed of ITO.

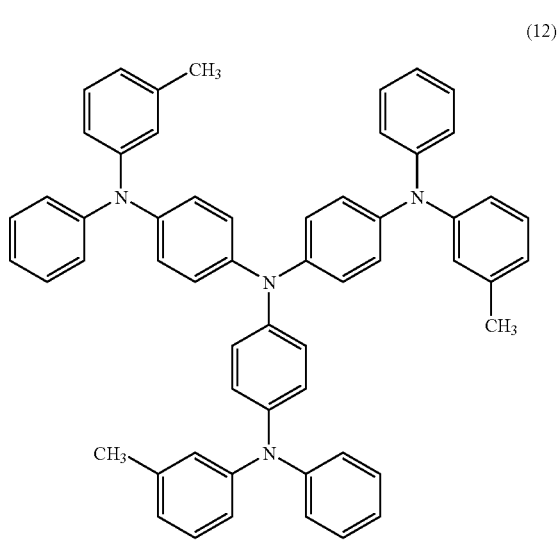

(12)

Then, the hole transport layer 4 composed of 4,4'-bis[N-(1-naphthyl)-N-phenyl-amino]biphenyl (hereinafter abbreviated as NPB) represented by a formula (13) shown below is formed on the above described hole injection layer 3.

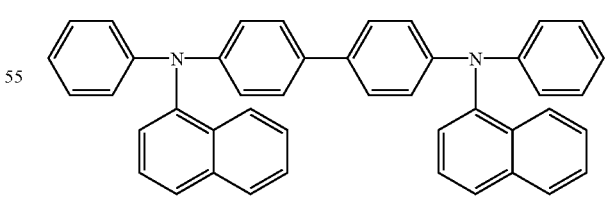

(13)

Thereafter formed on the hole transport layer 4 is the mixture luminescent layer 5 constituted by mixing three components being 4,4',4"-tri(N-carbazolyl)triphenylamine (hereinafter abbreviated as TCTA) represented by a formula (6) shown below, fac-tris(2-phenylpyridine)iridium (hereinafter abbreviated as Ir(ppy)) represented by a formula (8) shown below and DCJTB represented by a formula (10) shown below.

(6)

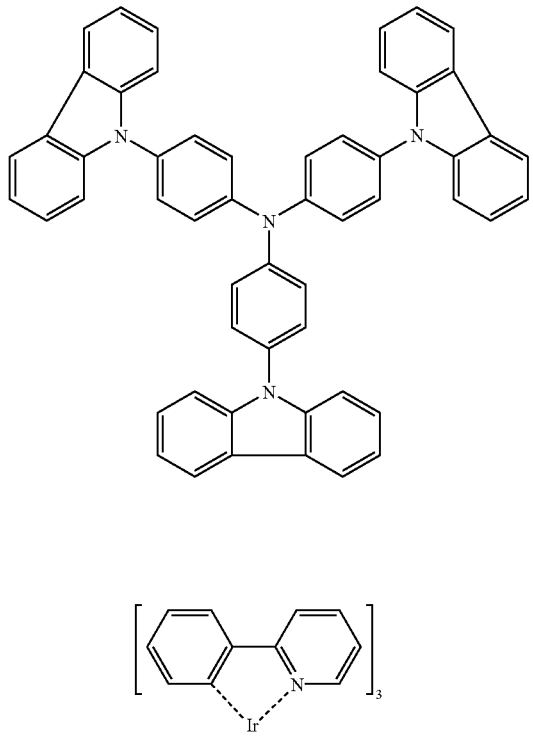

(8)

(10)

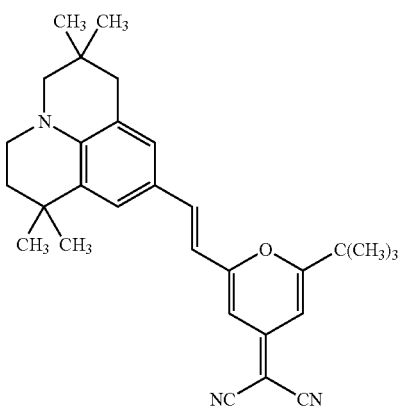

The average content of each component of the mixture luminescent layer 5 is that TCTA is 90.0 mass %, Ir(ppy) is 6.0 mass %, and DCJTB is 4.0 mass %.

The mixture luminescent layer 5 contains TCTA as a molecular substance, Ir(ppy) as a substance which emits light through a triplet excited state, and DCJTB as a luminescent substance which emits the light of a spectral component in the wavelength range of red.

Then, the hole blocking layer 6 composed of 2,9-dimethyl-4,7-diphenyl-1,10-phenanthroline (hereinafter abbreviated as BCP) represented by a formula (14) shown below is formed on the above mixture luminescent layer 5.

(14)

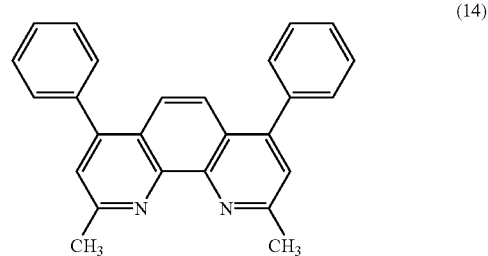

In addition, the electron injection layer 7 composed of aluminum tris(8-hydroxyquinoline) (hereinafter abbreviated as Alq) represented by a formula (15) shown below is formed on the hole blocking layer 6.

(15)

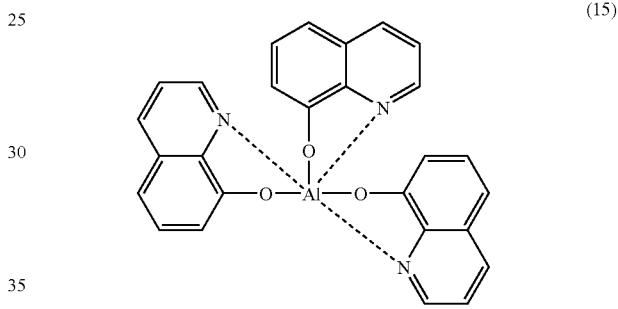

After the formation of each of the layers 3 to 7 as described above, the cathode 8 composed of a magnesium alloy (Mg:In) which contains indium of 10 mass % is formed on the electron injection layer 7 by a vapor deposition method.

In the foregoing manner, the organic thin film layer 10 constituted by the five stacked layers, which are the hole injection layer 3, the hole transport layer 4, the mixture luminescent layer 5, the hole blocking layer 6 and the electron injection layer 7 is formed to fabricate the organic EL element 100.

The film thickness of each of the layers 3 to 7 evaluated by a quartz crystal oscillator type film thickness meter is 25 nm, 10 nm, 25 nm, 17 nm and 20 nm, respectively. The film thickness of the anode 2 and that of the cathode 8 are 150 nm and 200 nm, respectively.

In the fabrication of the organic EL device 100 in the form of Example 1, constituent materials for the respective layers 3 to 7 are sublimated to form the respective layers 3 to 7 by a vapor deposition method, so as to form the organic thin film layer 10. It is thus unnecessary to use detrimental organic solvents to form the organic thin film layer 10. Also, it is possible to easily form each layer 3 to 7 with a uniform film thickness.

Figure 2:
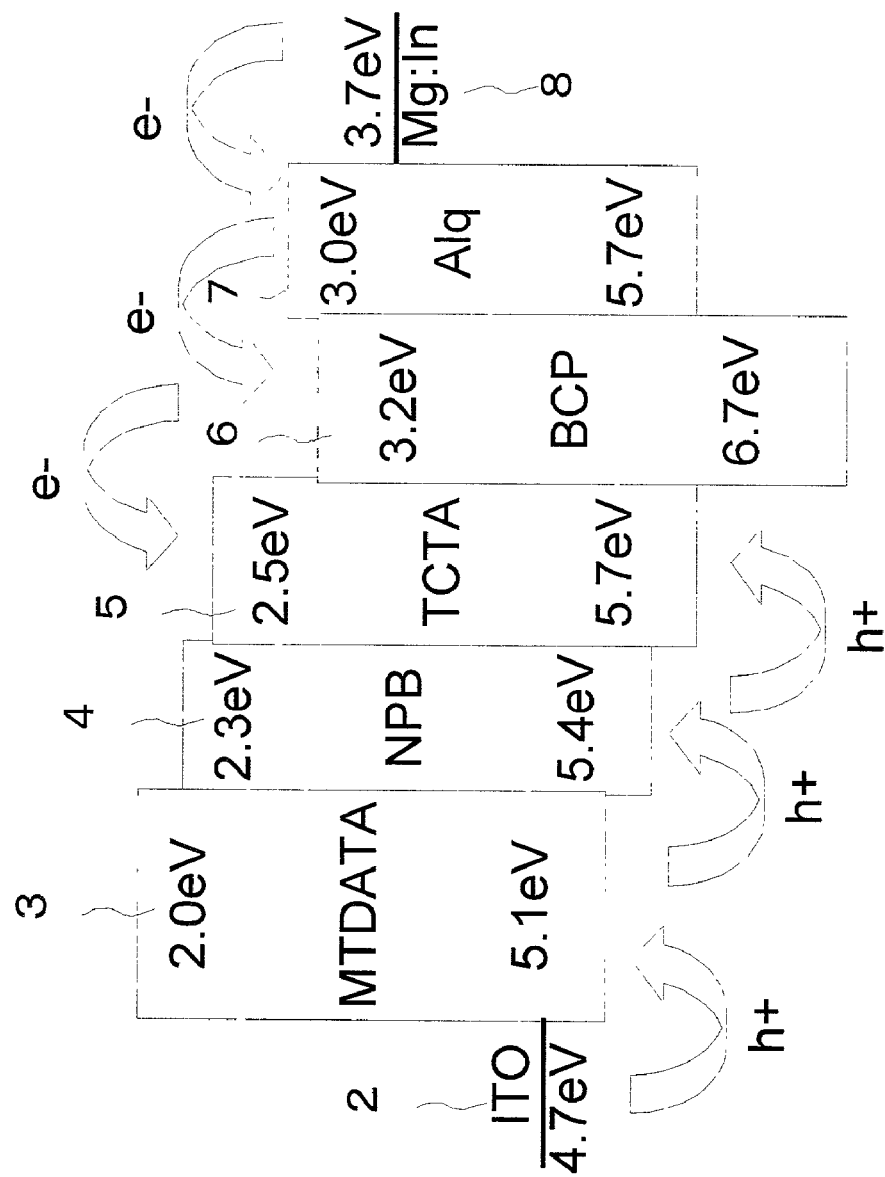
FIG. 2 is a diagram showing an energy level of a lowest unoccupied molecular orbital (LUMO) and that of a highest occupied molecular orbital (HOMO) of each layer of the organic EL device of Example 1, and a transfer process of electrons (e−) and holes (h+) in the organic EL device.

FIG. 2 is a diagram showing an energy level of a lowest unoccupied molecular orbital (LUMO) and that of a highest occupied molecular orbital (HOMO) of each layer 3 to 7 in the organic EL device 100, and a transfer process of electrons (e−) and holes (h+) therein.

A simplified molecular formula for MTDATA constituting the hole injection layer 3 is $C_{57}H_{48}N_4$. These numerals given in the simplified molecular formula denote the number of atoms in the molecule. MTDATA has a molar mass of 789.04 g/mol, a melting point of 203 and a glass transition temperature of 75° C. As shown in FIG. 2, MTDATA has an ionization potential of 5.1 eV, an electron affinity of 2.0 eV and an energy gap of 3.1 eV between HOMO and LUMO.

A simplified molecular formula for NPB constituting the hole transport layer 4 is $C_{44}H_{32}N_2$. NPB has a molar mass of 588.75 g/mol, a melting point of 277° C. and a glass transition temperature of 96° C. As shown in FIG. 2, NPB has an ionization potential of 5.4 eV, an electron affinity of 2.3 eV and an energy gap of 3.1 eV between HOMO and LUMO.

A simplified molecular formula for TCTA constituting the mixture luminescent layer 5 is $C_{54}H_{36}N_4$. TCTA has a molar mass of 740.91 g/mol, a melting point of 270° C. and a glass transition temperature of 151° C. As shown in FIG. 2, TCTA has an ionization potential of 5.7 eV, an electron affinity of 2.5 eV and an energy gap of 3.2 eV between HOMO and LUMO.

The mixture luminescent layer 5 includes Ir(ppy) and DCJTB other than TCTA as described in the foregoing, though their illustration is omitted in FIG. 2. A simplified molecular formula for Ir(ppy) is $C_{33}H_{24}N_3$ Ir. Ir(ppy) has a molar mass of 654.78 g/mol. A simplified molecular formula for DCJTB is $C_{30}H_{35}ON_3$. DCJTB has a molar mass of 453.62 g/mol.

A simplified molecular formula for BCP constituting the hole blocking layer 6 is $C_{26}H_{20}N_2$. BCP has a molar mass of 360.45 g/mol and a melting point of 279° C. to 283° C. As shown in FIG. 2, BCP has an ionization potential of 6.7 eV, an electron affinity of 3.2 eV and an energy gap of 3.5 eV between HOMO and LUMO.

In this case, the difference between the ionization potential (6.7 eV) of BCP constituting the hole blocking layer 6 and the ionization potential (5.7 eV) of TCTA constituting the mixture luminescent layer 5 is as very large as 1.0 eV. Also, the energy barrier between the hole blocking layer 6 composed of BCP and the mixture luminescent layer 5 composed of TCTA is as very large as 1.0 eV. This makes it possible to prevent holes from being injected from the mixture luminescent layer 5 into the hole blocking layer 6 and thus allows the holes to be stored in the mixture luminescent layer 5, as will be described later.

A simplified molecular formula for Alq constituting the electron injection layer 7 is $C_{27}H_{18}N_3O_3$ Al. Alq has a molar mass of 459.4318 g/mol, no melting point, a thermal cracking temperature of 412° C., and a glass transition temperature of 175° C. As shown in FIG. 2, Alq has an ionization potential of 5.7 eV, an electron affinity of 3.0 eV and an energy gap of 2.7 eV between HOMO and LUMO.

In the organic EL device 100, the ionization potential of the anode 2 is 4.7 eV, and the electron affinity of the cathode 8 is 3.7 eV, as shown in FIG. 2.

In the organic EL device 100, the holes injected from the anode 2 composed of ITO are transmitted through the hole injection layer 3 and the hole transport layer 4 in turn to the mixture luminescent layer 5. Since the respective energy barriers between the anode 2 and the hole injection layer 3, between the hole injection layer 3 and the hole transport layer 4, and between the hole transport layer 4 and the mixture luminescent layer 5 are as very small as from 0.3 eV to 0.4 eV, in the organic EL device 100, the holes injected from the anode 2 are easily transmitted to the mixture luminescent layer 5.

In this case, since the energy barrier between the mixture luminescent layer 5 and the hole blocking layer 6 is as large as described above, the holes are prevented from being injected from the mixture luminescent layer 5 into the hole blocking layer 6, and are stored in the mixture luminescent layer 5.

On the other hand, the electrons injected from the cathode 8 composed of Mg and In are transmitted through the electron injection layer 7 and the hole blocking layer 6 in turn to the mixture luminescent layer 5. In this case, since each energy barrier between the cathode 8 and the electron injection layer 7, between the electron injection layer 7 and the hole blocking layer 6 and between the hole blocking layer 6 and the mixture luminescent layer 5 is comparatively as small as from 0.2 eV to 0.7 eV, the electrons injected from the cathode 8 are comparatively easily transmitted to the mixture luminescent layer 5.

Those holes and electrons transmitted to the mixture luminescent layer 5 as described above are coupled to each other at the mixture luminescent layer 5. This causes TCTA within the mixture luminescent layer 5 to emit light through a singlet excited state.

Since such TCTA constituting the mixture luminescent layer 5 has the large energy gap of 3.2 eV between HOMO and LUMO, a spectral component in the wavelength range of blue or a spectral component in the range of a shorter wavelength than that of blue can emit light in the TCTA. In this case, an absorption edge wavelength on the side of the longest wavelength in an optical absorption spectrum in a visible light range of TCTA is around 390 nm.

The blue here means a color in the range of x<0.17 and y<0.4 in a CIE (Commission International d'Eclairage) chromaticity coordinate where x is an abscissa of the coordinate, and y is an ordinate thereof.

For example, TCTA has a larger energy gap between HOMO and LUMO than CBP which has been employed by Forrest, Stephen R. et al. set forth in the Description of the Background Art. The energy gap of CBP is 3.1 eV, whereas that of TCTA is 3.2 eV.

In addition, while the absorption edge wavelength on the side of the longest wavelength in the optical absorption spectrum in the visible light range of CBP is around 400 nm, the absorption edge wavelength on the side of the longest wavelength of TCTA is located at a shorter wavelength than that of CBP, specifically around 390 nm.

From the foregoing, blue light emission, which could not be realized in CBP, can be realized in such TCTA.

Furthermore, particularly in this case, since there is a large difference between the ionization potential of TCTA constituting the mixture luminescent layer 5 and that of BCP constituting the hole blocking layer 6 and thus a large energy gap between the mixture luminescent layer 5 and the hole blocking layer 6, the holes can be stored in the mixture luminescent layer 5, as described above. Thus, the holes and electrons are efficiently coupled to each other in the mixture luminescent layer 5 composed of TCTA. This makes it possible to realize blue light emission at excellent luminous efficiency in the mixture luminescent layer 5 composed of TCTA.

Consideration will now be made on a comparative case where the mixture luminescent layer 5 is composed of CBP, which has been described in the background art, in place of TCTA. In this case, the ionization potential of CBP is 6.3 eV which is higher than that of TCTA (5.7 eV). Accordingly, in this case, the difference between the ionization potential (6.3 eV) of CBP constituting the mixture luminescent layer 5 and that (6.7 eV) of BCP constituting the hole blocking layer 6 is 0.4 eV, which is smaller than the difference (1.0 eV) in ionization potential in the case where TCTA is employed.

Thus, the energy barrier provided between the mixture luminescent layer 5 and the hole blocking layer 6 is smaller in the case where CBP is employed for the mixture luminescent layer 5 as compared to the case where TCTA is employed for the mixture luminescent layer 6. The holes are thus liable to be injected from the mixture luminescent layer 5 into the hole blocking layer 6. This causes degradation in coupling efficiency between the holes and electrons in the mixture luminescent layer 5. Consequently, the luminous efficiency of the mixture luminescent layer 5 employing CBP becomes lower than that of the layer 5 employing TCTA.

The TCTA constituting the mixture luminescent layer 5 includes 4 nitrogen atoms. Such TCTA including a large number of nitrogen atoms achieves higher transportability of holes as compared to, for example, the above described CBP including 2 nitrogen atoms. Thus, the improved luminous efficiency of blue light emission is accomplished in the mixture luminescent layer 5 composed of such TCTA.

In the mixture luminescent layer 5 of the organic EL device 100, the holes and electrons are coupled to each other as described above, thereby causing excitation of TCTA. A part of energy is transferred from the excited TCTA to Ir(ppy), thereby causing excitation of Ir(ppy). Consequently, Ir(ppy) emits green light through a triplet excited state.

Green here indicates a color existing in the range of x<0.25 and y>0.6 in a chromaticity coordinate.

According to quantum mechanical studies, it is considered that out of the entire excited state caused by coupling of electrons and holes, the triplet excited state where electron spin is parallel is produced at a ratio of approximately 3/4, while the singlet excited state where electron spin is reverse parallel and the sum of spin quantum numbers is 0 is produced at a ratio of approximately 1/4.

The light emission which is caused when electrons being in the singlet excited state out of such two types of excited states transit to a ground state is called fluorescence. Such fluorescence is generated based on a spin allowable state and easily occurs. Thus, the fluorescence is applied in wide use for luminescent phenomena such as fluorescent substances, organic EL devices and the like.

On the other hand, the light emission which is caused when electrons being in the triplet excited state transit to the ground state is called phosphorescence. Such phosphorescence is generated based on a spin inhibited state, and according to Pauli's exclusion principle, it is not possible that two electrons with parallel electron spin exist on the same electron orbit (which corresponds to the ground state in this case). Therefore, the electron spin of electrons which may transit is required to be inverted by receiving perturbation of some kind, in order for the electrons being in the triplet excited state to transit to the ground state and emit light.

However, the inversion of electron spin is difficult in fluorescent substances and most of substances which are usually used for organic EL devices. Accordingly, phosphorescence is known as a special phenomenon which is observed only in a very low temperature area equal to or below a liquid nitrogen temperature as to normal substances. Thus, it is usually difficult to effectively utilize the triplet excited state covering approximately 3/4 of the entire excited state.

In contrast, as for the above described organic EL device 100, the mixture luminescent layer 5 includes Ir(ppy) which emits light through the triplet excited state. This allows Ir(ppy) to emit light through the triplet excited state which has not usually effectively been utilized irrespective of light emission, in the mixture luminescent layer 5. Since it is possible in this case to cause Ir(ppy) to emit green light by effective use of the triplet excited state covering approximately 3/4 of the entire excited state, luminous efficiency of Ir(ppy) is greatly increased.

In the mixture luminescent layer 5 of the organic EL device 100, energy is transferred from the excited TCTA and Ir(ppy) to DCJTB, thereby causing excitation of DCJTB. This makes DCJTB emit red light through the singlet excited state. This DCJTB can emit red light at excellent luminous efficiency as compared to such DCM2 and PtOEP as employed by Forrest, Stephen R. et al. described in the background art.

Red here indicates a color existing in the range of x>0.5 and 0.2<y<0.45 at the CIE chromaticity coordinate.

As has been described above, it is possible in the mixture luminescent layer 5 of the above described organic EL device 100 to obtain blue light emission of TCTA, green light emission of Ir(ppy) and red light emission of DCJTB at excellent luminous efficiency. Thus, it becomes possible in such mixture luminescent layer 5 to realize white light emission at excellent luminous efficiency by mixing of respective lights emitted from TCTA, Ir(ppy) and DCJTB. This makes it possible to obtain white light emission at excellent luminous efficiency in the organic EL device 100.

By the way, TCTA which is a principal component of the mixture luminescent layer 5 has a high glass transition point of 151° C., as described above. For example, although the glass transition temperature of CBP employed by Forrest, Stephen R. et al. described in the background art is not clear, it is presumed that CBP has a lower glass transition temperature than that of TCTA because of the difference in molecular structure between CBP and TCTA.

TCTA with such a high glass transition temperature has such properties that it retains an amorphous state at a lower temperature area than 151° C. being its glass transition temperature, as disclosed in Japanese Patent Laid Open No. 3-232856. Thus, in the mixture luminescent layer 5 of the organic EL device 100 principally composed of such TCTA, the TCTA contained in the mixture luminescent layer 5 is not crystallized even if the ambient temperature of the organic EL device 100 rises up to a high temperature area below the glass transition temperature.

This makes it possible to avoid deviations in electric conductivity and short-circuits due to crystallization of TCTA contained in the mixture luminescent layer 5. This effects an increase in heat resistivity of the organic EL device 100 without any destruction of the device even if the temperature of the device rises up to the high temperature area below the glass transition temperature.

In addition, TCTA being a principal component of the mixture luminescent layer 5 includes 4 nitrogen atoms and 54 carbon atoms as described above, and its molar mass is as large as 740.91 g/mol. For example, such CBP as described in the background art includes 36 carbon atoms and has a 484.60 g/mol molar mass, so that TCTA includes much more carbon atoms and has a larger molar mass than those of CBP.

Such TCTA with a large number of carbon atoms and a large molar mass has its heat resistivity greatly increased as compared to that of CBP. Accordingly, the organic EL device 100 having the mixture luminescent layer 5 composed of such TCTA has its heat resistivity greatly increased.

In general, the energy gap between HOMO and LUMO is liable to be smaller in a case where the number of carbon atoms in molecules increases and in a case where a molar mass of molecules increases. In contrast, TCTA has such a large energy gap as describe above along with a large number of carbon atoms and a large molar mass. This makes it possible to achieve blue light emission in TCTA together with an increased heat resistivity.

As described in the foregoing, it is possible to obtain white light emission with excellent luminous efficiency and realize a thin light emitting device with excellent heat resistivity in the organic EL device 100 of Example 1. This organic EL device 100 is applicable to various fields such as full-color displays and the like.

Detailed description will now be made on a case where white light emission is obtained from the organic EL device 100.

When the above organic EL device 100 was energized with application of a direct current voltage of 29 V, a current density was 0.34 mA/cm$^2$, white light emission with a 1.2 cd/m$^2$ luminance was obtained, a chromaticity coordinate in a CIE x-y chromaticity coordinate system was (x=0.20, y=0.22), and a current luminous efficiency attained at this time was 0.35 cd/A.

When the device was energized with application of the direct current voltage of 35 V, the current density was 2.4 mA/cm$^2$, white light emission with a 10 cd/m$^2$ luminance was obtained, the chromaticity coordinate was (x=0.20, y=0.23), and the current luminous efficiency attained at this time was 0.42 cd/A.

When the device was energized with application of the direct current voltage of 40 V, the current density was 7.8 mA/cm$^2$, white light emission with a 34 cd/m$^2$ luminance was obtained, the chromaticity coordinate was (x=0.20, y=0.24), and the current luminous efficiency attained at this time was 0.44 cd/A.

When the device was energized with application of the direct current voltage of 44 V, the current density was 24 mA/cm$^2$, white light emission with a 105 cd/m$^2$ luminance was obtained, the chromaticity coordinate was (x=0.20, y=0.26), and the current luminous efficiency attained at this time was 0.44 cd/A.

When the device was energized with application of the direct current voltage of 45 V, the current density was 29 mA/cm$^2$, white light emission with a 130 cd/m$^2$ luminance was obtained, the chromaticity coordinate was (x=0.20, y=0.26), and the current luminous efficiency attained at this time was 0.45 cd/A.

As described above, such tendency was observed that the current luminous efficiency has slowly increased along with the increased luminance in the organic EL device 100 of Example 1. This is a very preferable characteristic for the organic EL device 100 to be put in practical use.

Moreover, while it was observed that the current luminous efficiency had a tendency to increase along with the increased luminance as described above in the area of a luminance of 8 cd/m$^2$ or more, it was understood that the luminance was roughly in proportion to the current density, and a proportional coefficient provided in this case was correspondent to the current luminous efficiency. From those observations, it was confirmed that adjustment of the current density made it possible and much easier to control the luminance in the above organic EL device 100.

Analysis was then made on the spectral component of the white light emission obtained when the above organic EL device 100 was energized with application of the direct current voltage of 35 V. Consequently, it was apparent that the strongest luminescence peak existed at a 440 nm wavelength, and luminescence peaks also existed at around 540 nm and 700 nm wavelengths, respectively. In this case, the intensity ratio of the respective luminescence peaks was as follows: the 440 nm peak:the 540 nm peak:the 700 nm peak=61.2:26.6:12.2.

From the comparison with data of a photo-excitation luminance (PL) spectrum, it is considered that the luminescence peak of the 440 nm wavelength results from the emission from TCTA, the luminescence peak of the 540 nm wavelength results from the emission from Ir(ppy), and the luminescence peak of around the 700 nm wavelength results from the emission from the DCJTB. Thus, it was apparent that the blue light emission from TCTA is a principal constituent component of the spectral component of the white light emission obtained from the device, in the mixture luminescent layer 5 of the above organic EL device 100.

In addition, after the above organic EL device 100 was kept in an oven at 65° C. for one hour, the device was then taken out of the oven and was allowed to cool. After that, the device was again made emitting light, so that the same white light emission as the one obtained before put into the oven was obtained. As described above, deterioration in luminescent characteristics was not particularly observed in the organic EL device 100 even though the peripheral temperature of the device was raised. From this observation, it was able to be considered that the above organic EL device 100 had a heat resistivity of up to at least about 70° C.

Example 2

An organic EL device in Example 2 of the present invention has the same structure as that of the above described organic EL device 100 in Example 1 except that it is different from the device 100 in Example 1 in the constituent of a mixture luminescent layer. Respective film thicknesses of an anode, a hole injection layer, a hole transport layer, a mixture luminescent layer, a hole blocking layer, an electron injection layer and a cathode included in the organic EL device of Example 2, which are evaluated by a quartz crystal oscillator type film thickness meter, are 150 nm, 25 nm, 10 nm, 25 nm, 17 nm, 20 nm and 200 nm, respectively, like those of the organic EL device 100 of Example 1.

The organic EL device in Example 2 includes a mixture luminescent layer composed of a mixture containing two components, TCTA and Ir(ppy). The average content of each component contained in the mixture luminescent layer of the organic EL device in Example 2 is as follows: 94.0 mass % for TCTA, and 6.0 mass % for Ir(ppy).

In such a mixture luminescent layer of the organic EL device, TCTA is contained as a molecular substance, and Ir(ppy) is contained as a substance emitting through a triplet excited state.

Like the organic EL device 100 in Example 1, it is possible to obtain blue light emission of TCTA and green light emission of Ir(ppy) in the mixture luminescent layer at excellent luminous efficiency in the organic EL device in Example 2. This makes it possible to obtain white light at excellent luminous efficiency by mixing both of the light emitted from TCTA and Ir(ppy) in the organic EL device in Example 2. Such an organic EL device is applicable to various fields such as full-color displays and the like.

Moreover, since the mixture luminescent layer of the organic EL device in Example 2 is mainly composed of TCTA having a high glass transition point and a large molar mass like the organic EL device 100, its heat resistivity can be increased in the mixture luminescent layer. Accordingly, the heat resistivity can be increased in the organic EL device having such a mixture luminescent layer.

Detailed description will now be made on a case where white light emission was obtained from the organic EL device of Example 2.

When the organic EL device of Example 2 was energized with application of a 30 V direct current voltage, a current density was 0.40 mA/cm$^2$, white emission with a 1.25 cd/m$^2$ luminance was obtained, a chromaticity coordinate in a CIE x-y chromaticity coordinate system was (x=0.20, y=0.25), and a current luminous efficiency at this time was 0.31 cd/A.

When the organic EL device was energized with application of a 35 V direct current voltage, the current density was 2.1 mA/cm$^2$, white light emission with a 7.4 cd/m$^2$ luminance was obtained, the chromaticity coordinate was (x=0.18, y=0.25), and the current luminous efficiency at this time was 0.35 cd/A.

When the device was energized with application of a 36 V direct current voltage, the current density was 2.8 mA/cm$^2$, white light emission with a 10 cd/m$^2$ luminance was obtained, the chromaticity coordinate was (x=0.15, y=0.24), and the current luminous efficiency at this time was 0.37 cd/A.

As described above, it was viewed that the current luminous efficiency had a tendency to be increased slowly with the increased luminance in the organic EL device of Example 2. This is a very preferable characteristic for the organic EL device to be put in practical use.

When the above organic EL device was energized with application of an approximately 37 V direct current voltage, white light emission with a greenish tint was obtained. Analyzing a spectral component of the obtained white light emission, the most intense luminescence peak existed at a 450 nm wavelength, and then another luminescence peak also existed at around a 570 nm wavelength. In this case, assuming the intensity of the luminescence peak at the 570 nm wavelength was 1, then the intensity of the luminescence peak at the 450 nm wavelength was approximately 2.0 to 2.6.

From the comparison with data of photo-excitation luminescence (PL), the luminescence peak at the 450 nm wavelength is considered to be the emission from TCTA, and the luminescence peak at the 570 nm wavelength is considered to be the emission form Ir(ppy). It is thus apparent that the blue emission from TCTA is a principal constituent component of the spectral component of the white emission obtained from the device in the mixture luminescent layer of the above organic EL device.

While the foregoing description has been made on the case where the luminescent layer composed of the mixture containing TCTA and Ir(ppy) is formed in the above organic EL devices of Examples 1 and 2, a luminescent layer composed of only TCTA may be formed. In such case, an organic EL device capable of emitting blue light at high luminous efficiency can be achieved.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An organic light emitting device, comprising:
   an anode;
   a cathode; and
   a luminescent substance placed between said anode and said cathode, comprising:
   a first molecular substance in which an absorption edge of the longest wavelength in an optical absorption spectrum is less than 400 nm, said first molecular substance having a structure represented by a general formula (2) shown below

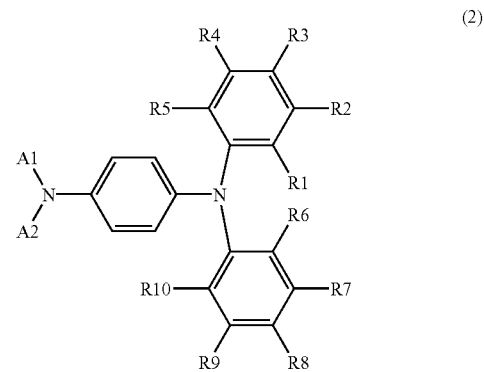

(2)

where R1 to R10 are identical to or different from one another each representing a hydrogen atom or a substituent; R1 and R6 may be bonded to each other to form a ring; adjacent ones of R1 to R5 and adjacent ones of R6 to R10 may be bonded to each other to form rings; and A1 and A2 are identical to or different from each other each representing a hydrogen atom or a substituent; and a second molecular substance emitting the light of the spectral component in the wavelength range of red, which is 2-(1,1-Dimethylethyl)-6-(2-(2,3,6,7-tetrahydro-1,1,7,7-tetramethyl-1H, 5H-benzo(ij)quinolizin-9-yl)ethenyl)-4H-pyran-4H-y-lidene)propanedinitrile represented by a formula (10) shown below

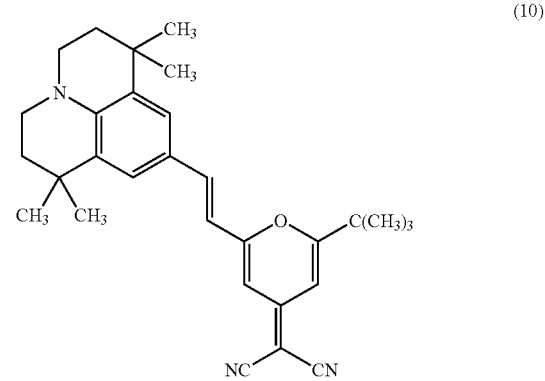

(10)

wherein said luminescent substance further includes a substance emitting light through a triplet excited state, and wherein the organic light emitting device makes blue or white emission.

2. The organic light emitting device according to claim 1, wherein
said first molecular substance has an ionization potential lower than an ionization potential of 4,4'-bis(carbazol-9-yl)biphenyl.

3. The organic light emitting device according to claim 1, wherein
said first molecular substance has an ionization potential of 6.2 eV or less.

4. The organic light emitting device according to claim 1, wherein
said first molecular substance has a molar mass of 486 g/mol or more.

5. The organic light emitting device according to claim 1, wherein
said first molecular substance contains 3 or more nitrogen atoms per molecule.

6. The organic light emitting device according to claim 1, wherein
said first molecular substance contains 37 or more carbon atoms per molecule.

7. The organic light emitting device according to claim 1, wherein said first molecular substance has a melting point higher than that, or a glass transition temperature higher than that, of 4,4'-bis(carbazol-9-yl)biphenyl.

8. The organic light emitting device according to claim 1, wherein
at least one of said A1 and A2 in said first molecular substance is a group represented by a general formula (3) shown below

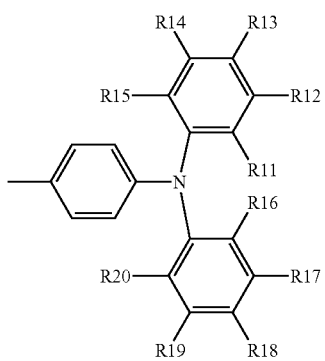

(3)

where R11 to R20 are identical to or different from one another each representing hydrogen atom or substituent; R11 and R16 may be bonded to each other to form a ring; adjacent ones of R11 to R15 and adjacent ones of R16 to R20 may be bonded to each other to form rings; and R11 to R20 may be identical to or different from R1 to R10.

9. The organic light emitting device according to claim 1, wherein
said first molecular substance includes a carbazol-9-yl structure represented by a general formula (4) shown below

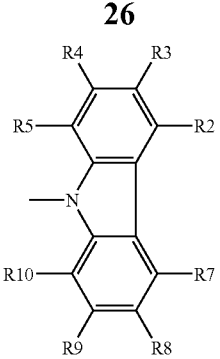

(4)

where R2 to R5 and R7 to R10 are as defined in claim 1.

10. The organic light emitting device according to claim 8, wherein
said first molecular substance includes a carbazol-9-yl structure represented by a general formula (5) shown below

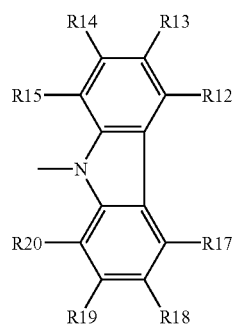

(5)

where R12 to R15 and R17 to R20 are as defined in claim 8.

11. The organic light emitting device according to claim 9, wherein said first molecular substance includes 3 or more carbazol-9-yl structures represented by said formula (4) per molecule.

12. The organic light emitting device according to claim 1, wherein
said first molecular substance is 4,4',4''-tri (N-carbazolyl) triphenylamine represented by a formula (6) shown below (6)

13. The organic light emitting device according to claim 1, wherein
said substance emitting light through the triplet excited state is a substance including an element of atomic number 56 or more.

14. The organic light emitting device according to claim 1, wherein
said substance emitting light through the triplet excited state is a substance including an element of atomic number 76 or more.

15. The organic light emitting device according to claim 1, wherein
said substance emitting light through the triplet excited state includes at least one selected from the group consisting of Group 8 element, Group 9 element, Group 10 element and Group 11 element of the Periodic Table of Elements.

16. The organic light emitting device according to claim 1, wherein
said substance emitting light through the triplet excited state includes at least one selected from the group consisting of osmium, iridium, platinum and gold.

17. The organic light emitting device according to claim 1, wherein said substance emitting light through the triplet excited state includes iridium.

18. The organic light emitting device according to claim 1, wherein
said substance emitting light through the triplet excited state has a structure represented by a general formula (7) shown below

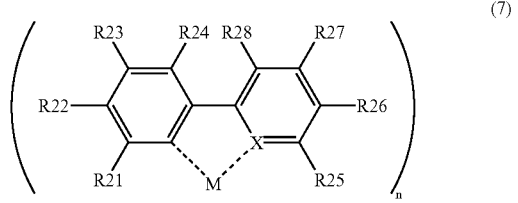

(7)

where M represents a metal atom and X represents a nonmetal atom; R21 to R28 are identical to or different from one another representing a hydrogen atom or a substituent; R24 and R28 may be bonded to each other to form a ring; adjacent ones of R21 to R24 may be bonded to each other to form a ring, and adjacent ones of R25 to R28 may be bonded to each other to form a ring; and n represents an integer of from 1 to 4.

19. The organic light emitting device according to claim 1, wherein
said substance emitting light through the triplet excited state is fac-tris (2-phenylpyridine) iridium represented by a formula (8) shown below

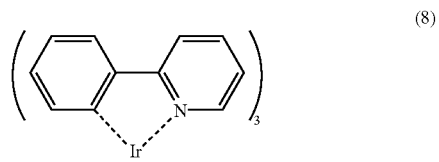

(8)

20. The organic light emitting device according to claim 1, wherein
said substance emitting light through the triplet excited state emits the light of a spectral component in the wavelength range of green and/or red.

21. The organic light emitting device according to claim 1, wherein
said luminescent substance is formed by a vacuum vapor deposition method.

22. The organic light emitting device according to claim 1,
said luminescent substance is included in a luminescent layer provided between said anode and said cathode.

* * * * *